US012601004B2

(12) United States Patent  
Sanders et al.

(10) Patent No.: US 12,601,004 B2  
(45) **Date of Patent: \*Apr. 14, 2026**

(54) DEPLETION PROBES

(71) Applicant: Watchmaker Genomics, Inc., Boulder, CO (US)

(72) Inventors: Travis J. Sanders, Boulder, CO (US); Martin Ranik, Boulder, CO (US); Brian A. Kudlow, Boulder, CO (US)

(73) Assignee: Watchmaker Genomics, Inc., Boulder, CO (US)

( * ) Notice: Subject to any disclaimer, the term of this patent is extended or adjusted under 35 U.S.C. 154(b) by 524 days.

This patent is subject to a terminal disclaimer.

(21) Appl. No.: 18/116,013

(22) Filed: Mar. 1, 2023

(65) Prior Publication Data

US 2023/0279467 A1 Sep. 7, 2023

Related U.S. Application Data

(60) Provisional application No. 63/315,131, filed on Mar. 1, 2022.

(51) Int. Cl.
| | |
|---|---|
| *C12Q 1/68* | (2018.01) |
| *C12N 15/10* | (2006.01) |
| *C12Q 1/6806* | (2018.01) |
| *C12Q 1/6876* | (2018.01) |

(52) U.S. Cl.
CPC ....... *C12Q 1/6806* (2013.01); *C12N 15/1003* (2013.01); *C12Q 1/6876* (2013.01)

(58) Field of Classification Search
None
See application file for complete search history.

(56) References Cited

U.S. PATENT DOCUMENTS

| | | | | |
|---|---|---|---|---|
| 11,421,216 B2* | 8/2022 | Kuersten | ............ | C12N 15/1024 |
| 2003/0108919 A1 | 6/2003 | Kautzer et al. | | |
| 2006/0228735 A1 | 10/2006 | Bobrow et al. | | |
| 2009/0325813 A1 | 12/2009 | Wang et al. | | |

(Continued)

FOREIGN PATENT DOCUMENTS

WO 2018/045181 A1 3/2018

OTHER PUBLICATIONS

International Preliminary Report on Patentability for Application No. PCT/US2023/063467, mailed Sep. 12, 2024.

(Continued)

*Primary Examiner* — Aaron A Priest
(74) *Attorney, Agent, or Firm* — Wolf, Greenfield & Sacks, P.C.

(57) ABSTRACT

The invention provides sets of RNA depletion probes, short DNA oligos that hybridize along the length of a target RNA and mediate digestion of the target RNA by RNase H to remove super-abundant RNA molecules from a sample. Depletion probes according to the invention are designed foremost based on biochemistry and the biophysical properties of the probes so that all of the depletion probes of a set exhibit substantially uniform, consistent behavior in binding to a target RNA in a sample. Probes are principally designed to specific performance targets and biophysical properties, yielding probe sets with irregular, even apparently random, spacing along a target RNA molecule.

12 Claims, 12 Drawing Sheets

(56)                    References Cited

U.S. PATENT DOCUMENTS

| 2011/0111409 A1* | 5/2011 | Sinicropi | .......... C12N 15/1003 |
| | | | 536/24.31 |
| 2013/0203057 A1 | 8/2013 | Lemieux et al. | |
| 2014/0093882 A1* | 4/2014 | Farmer | ............... C12Q 1/6848 |
| | | | 435/6.12 |
| 2015/0299771 A1 | 10/2015 | Sinicropi et al. | |
| 2020/0199572 A1 | 6/2020 | Kuersten et al. | |
| 2023/0279490 A1 | 9/2023 | Sanders et al. | |

OTHER PUBLICATIONS

[No Author Listed], "Random" definition and meaning. Dictionary. com. Accessed at: https://www.dictionary.com/browse/random; Last accessed: May 14, 2025. 7 pages.

Najam et al., Pattern Matching for DNA Sequencing Data Using Multiple Bloom Filters. Biomed Res Int. Apr. 14, 2019:2019:7074387. doi: 10.1155/2019/7074387. eCollection 2019.

Pruitt et al., NCBI reference sequences (RefSeq): a curated non-redundant sequence database of genomes, transcripts and proteins. Nucleic Acids Res. Jan. 2007;35(Database issue):D61-5. doi: 10.1093/nar/gk1842. Epub Nov. 27, 2006.

Rodriguez-Puente et al., Algorithm for shortest path search in Geographic Information Systems by using reduced graphs. SpringerPlus. Jul. 1, 2013 2:291. doi: 10.1186/2193-1801-2-291. eCollection 2013.

Schliep et al., Efficient Computational Design of Tiling Arrays Using a Shortest Path Approach. In: Algorithms in Bioinformatics. Springer-Verlag Berlin Heidelberg, eds. WABI 2007. pp. 383-394.

International Search Report and Written Opinion for Application No. PCT/US2023/063467, mailed Jun. 21, 2023.

Alkan et al., Ribo-ODDR: oligo design pipeline for experiment-specific rRNA depletion in Ribo-seq. Bioinformatics. Sep. 9, 2021;37(17):2659-2667. doi: 10.1093/bioinformatics/btab171.

Choe et al., RiboRid: A low cost, advanced, and ultra-efficient method to remove ribosomal RNA for bacterial transcriptomics. PLOS Genet. Sep. 2, 20217;17(9):e1009821. doi: 10.1371/journal.pgen.1009821. eCollection Sep. 2021.

Phelps et al., Optimized design of antisense oligomers for targeted rRNA depletion. Nucleic Acids Res. Jan. 1, 20211;49(1):e5. doi: 10.1093/nar/gkaa1072.

* cited by examiner

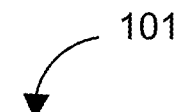
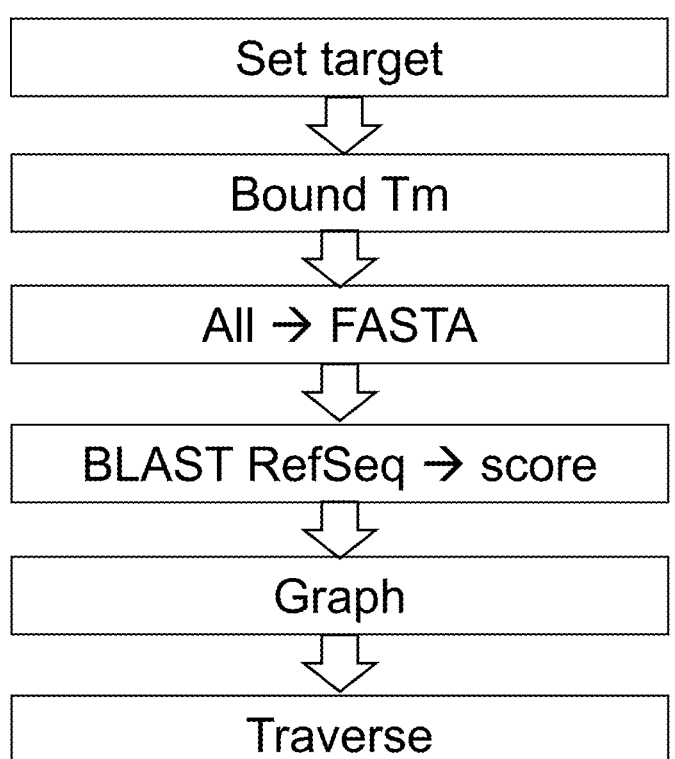
FIG. 1

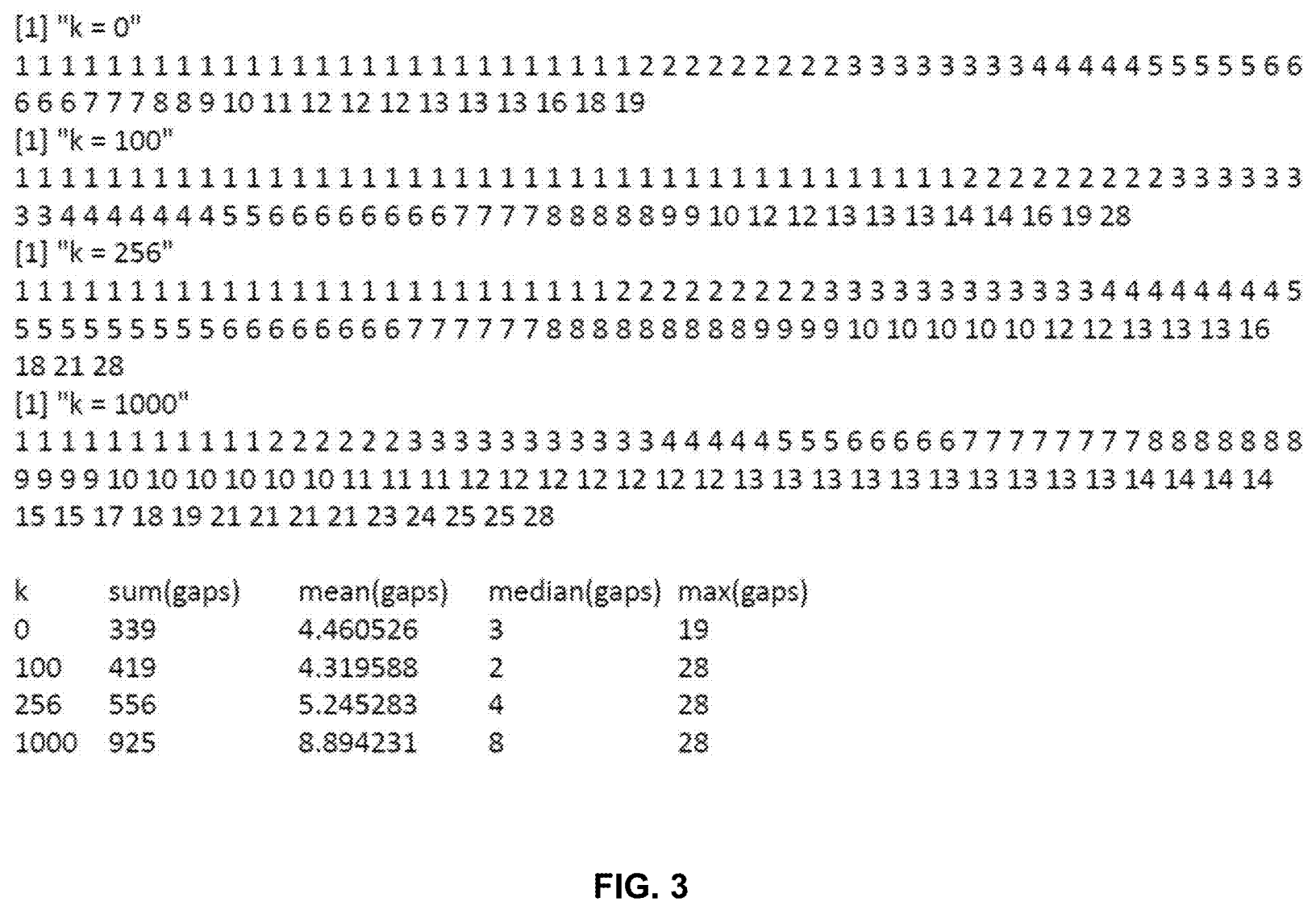

[1] "k = 0"
1 1 1 1 1 1 1 1 1 1 1 1 1 1 1 1 1 1 1 1 1 1 1 1 1 1 1 1 1 2 2 2 2 2 2 2 2 3 3 3 3 3 3 3 4 4 4 4 4 5 5 5 5 6 6
6 6 6 7 7 7 8 8 9 10 11 12 12 13 13 16 18 19

[1] "k = 100"
1 1 1 1 1 1 1 1 1 1 1 1 1 1 1 1 1 1 1 1 1 1 1 1 1 1 1 1 1 1 1 1 2 2 2 2 2 2 2 2 3 3 3 3 3 3
3 3 4 4 4 4 4 5 6 6 6 6 6 6 6 7 7 7 8 8 8 8 9 9 10 12 12 13 13 14 14 16 19 28

[1] "k = 256"
1 1 1 1 1 1 1 1 1 1 1 1 1 1 1 1 1 1 1 1 1 1 1 1 2 2 2 2 2 2 2 2 3 3 3 3 3 3 3 3 3 4 4 4 4 4 4 4 4 4 5
5 5 5 5 5 5 6 6 6 6 6 6 6 7 7 7 7 7 7 7 8 8 8 8 8 9 9 9 9 10 10 10 12 12 13 13 13 16
18 21 28

[1] "k = 1000"
1 1 1 1 1 1 1 1 2 2 2 2 2 2 2 3 3 3 3 3 3 3 3 3 4 4 4 4 4 5 5 5 6 6 6 6 6 6 7 7 7 7 7 7 7 7 8 8 8 8 8 8 8 8
9 9 9 10 10 10 10 10 11 11 11 12 12 12 12 12 13 13 13 13 13 13 14 14 14 14
15 15 17 18 19 21 21 21 23 24 25 25 28

| k | sum(gaps) | mean(gaps) | median(gaps) | max(gaps) |
| --- | --- | --- | --- | --- |
| 0 | 339 | 4.460526 | 3 | 19 |
| 100 | 419 | 4.319588 | 2 | 28 |
| 256 | 556 | 5.245283 | 4 | 28 |
| 1000 | 925 | 8.894231 | 8 | 28 |

FIG. 3

Human / Mouse / Rat (H/M/R) probe design

Algorithm design of depletion probes to human transcript target

Remove probes with high homology to undesired human transcript targets

Algorithm design of depletion probes to mouse/rat transcript targets

Remove probes with high homology to undesired mouse/rat transcript targets

Cross check human probes to mouse/rat transcriptome and vice versa

Remove probes with high homology to undesired transcript targets in H/M/R

FIG. 7

10 ng total RNA from FFPE 400 ng total RNA from FFPE ribosomal depletion of total RNA derived from universal Mouse and Rat references ■ % intergenic     % intronic     ■ % mRNA     ■ % rRNA

100%

75%

50%

25%

0%

Mouse before depletion     Mouse after depletion     Rat before depletion     Rat after depletion

DEPLETION PROBES

RELATED APPLICATIONS

This application claims the benefit under 35 U.S.C. 119 (e) of U.S. Provisional Application No. 63/315,131, filed on Mar. 1, 2022, the entire contents of which are incorporated herein by reference.

TECHNICAL FIELD

The disclosure relates to depletion probes.

BACKGROUND

The transcriptome refers to the RNA transcripts of a cell or organism at a given time. Knowledge of the transcriptome reveals active cellular processes and can provide information about cell regulation, growth and dysfunction.

Transcriptome analysis typically involves microarray technology and, more commonly, next-generation sequencing technologies (e.g., RNA-Seq). Common objectives of RNA-Seq are to detect all of the diverse transcripts present, including mRNA and non-coding RNA, as well as to detect splice variants, mutations, mobile genetic elements, and expression levels during various stages of development or under various conditions. Transcriptomics and RNA-Seq have application in diagnostics, disease profiling, pathogen detection, evolutionary biology, and other areas of research. For example, RNA-Seq can potentially identify genes involved in resistance to environmental stresses, such as drought resistance in crops. In another example, transcriptomic profiling can provide information on mechanisms of drug resistance, potentially revealing strategies for combating hospital-acquired antibiotic-resistant infections.

SUMMARY

The invention provides sets of RNA depletion probes, short DNA oligos that hybridize along the length of an RNA to be depleted from a sample. The DNA oligos mediate digestion of the target RNA by RNase H. The invention is useful to remove non-target RNA from a sample in order to promote capture of low abundance RNA or simply to achieve a higher yield of target RNA. Depletion probes according to the invention are designed based on the biochemistry and biophysical properties of probe/target interaction so that all of the depletion probes of a set exhibit uniform, consistent behavior. For example, the depletion probes may be designed to have a melting temperature (Tm) within a narrow, pre-defined range. Probes according to the invention are designed to achieve improved performance, often yielding probe sets with irregular, even apparently random, spacing along an RNA that is to be removed from a sample.

Regardless of the irregular spacing, probe sets of the invention outperform prior art probe sets due to the rational biology-based design that models Tm and screens reference RNA sequence data to omit candidate probe sequences with off-target matches. Prior art probe sets sacrifice complete deletion in order to achieve uniform probe binding along an RNA to be removed. Due to the limiting assumption that probe sets must tile along the length of the RNA with uniform spacing and melting temperature, a number of the probes bind poorly due to factors such as GC content, secondary structure, or length. The invention addresses those problems by using a design methodology that works within a selected window of melting temperatures and reduced off-target binding.

Probes of the invention form heteroduplexes along one or more RNA molecules with unpredictable, apparently random spacing. In fact, probe sets of the invention may leave long gaps of RNA—in some cases, gaps of up to more than about 100 bases—yet still outperform prior art probe sets designed to follow some simple pattern of short, regular gaps along the target RNA. In addition, probes of the invention show improved depletion even in highly degraded samples. Another advantage of probe design according to the invention is that it allows for probe hybridization and RNA digestion to occur in a single, rapid step as opposed to the use of heating/cooling cycles followed by a lengthy and suboptimal digestion temperature. Because probe sets of the invention use probes designed to exploit the actual sequence content and biophysical properties of heteroduplex formation, RNA depletion using probe sets of the invention reliably removes superabundant RNAs from a sample. Because such tools may be used to reliably remove RNAs, such as ribosomal RNAs and/or globin transcripts, RNA-Seq assays using probe sets of the invention better detect the remaining, and sometimes rare, mRNA transcripts. Because rare genetic events are markers of critical conditions, such as cancer or pathogenic infection, probe sets of the invention are useful for the early and accurate detection of critical biological information.

In certain aspects, the invention provides methods for depleting RNA. Preferred methods include hybridizing a plurality of DNA oligos to a target RNA molecule in a sample to form heteroduplexes, wherein the DNA oligos have sequences selected to (i) give the heteroduplexes melting temperatures within a predetermined range, and (ii) minimize matches to reference off-target RNAs. Methods of the invention further include digesting RNA in the heteroduplexes. The heteroduplexes may be formed with a non-uniform distribution along the RNA molecule. The DNA oligos may include low GC oligos and high GC oligos that have higher melting temperatures than the low GC oligos. The DNA oligos may include low GC oligos and high GC oligos that are shorter than the low GC oligos. The DNA oligos may be selected to minimize spacing between adjacent heteroduplexes and may be present in non-uniform concentrations.

In some embodiments, DNA oligos are selected by: generating a set of candidate sequences complementary to a target RNA (in this case, the RNA to be removed) with predicted melting temperatures within a predetermined range; assigning a cost function to each of the candidate sequences based at least in part on a match score to the reference off-target RNAs; and selecting a set of the candidate sequences that map to positions along the RNA molecule, wherein the set is selected by an algorithm that minimizes cumulative cost function, inter-position gaps, and/or overlap. The DNA sequences may be selected by a computer system to provide DNA oligos that each uniquely anneal to the RNA molecule with similar annealing temperatures, with minimal or no overlap, and with minimal or no annealing to off-target RNA. Optionally the computer system further selects the sequences to provide the DNA oligos with a minimum length and/or to minimize gaps between heteroduplexes.

In some embodiments, DNA oligos are tested and shown not to hybridize stably to protein coding transcripts in a standardized human reference RNA extract. The target RNA molecule may include any of a ribosomal RNA, a globin transcript, or a mitochondrial RNA. Preferred methods include performing the recited steps to digest ribosomal RNA and globin transcripts from the sample. The digesting step may include treating the sample with RNAseH. In addition, preferred methods may include, after the digesting step, reverse transcribing non-target RNA molecules from the sample. In preferred embodiments, the heteroduplexes are formed at positions along the RNA molecule that do not form any regular, repeating, or uniform pattern or spacing. E.g., spacing between the heteroduplexes may be highly variable and/mathematically random. Positioning of the heteroduplexes may leave one or more uncovered regions of the RNA molecule of at least about 10 to about 100 bases. Moreover, coverage need not be end to end, meaning that 5' and 3' end sequences may be uncovered.

Methods of the invention may increase a ratio of poly-A tailed RNA to non-coding RNA in the sample. Sequences of at least two of the DNA oligos are selected to hybridize to the RNA to be depleted at locations that overlap or abut one another. DNA oligos used in the invention may have lengths that vary from about 20 bases to about 40 bases (e.g., vary between 18 and 44 inclusive). The DNA oligos may be present in the mix at non-equimolar concentrations. For example, based on empirical observations, some of the probes may be boosted, e.g., doubled in concentration.

Aspects of the invention provide a set of RNA depletion probes. An exemplary set includes a plurality of DNA oligos that hybridize to an RNA to be depleted to form heteroduplexes, wherein the DNA oligos have sequences selected to (i) give the heteroduplexes melting temperatures within a predetermined range, and (ii) minimize matching to off-target RNA. Preferably the heteroduplexes are formed with a non-uniform distribution along the RNA molecule. Spacing between the heteroduplexes in the set may be highly variable and/or mathematically random. The DNA oligos may be selected to minimize spacing between adjacent heteroduplexes. The DNA oligos may include both low GC oligos and high GC oligos (that have higher melting temperatures than the low GC oligos and/or are shorter than the low GC oligos). The probe set may be designed by generating a set of candidate sequences complementary to the RNA molecule with predicted melting temperatures within the predetermined range; assigning a cost function to each of the candidate sequences based at least in part on a match score to the reference off-target RNAs; and selecting a set of the candidate sequences that map to positions along the RNA molecule, wherein the set is selected by an algorithm that minimizes cumulative cost function, inter-position gaps, and/or overlap. The probe set may be designed to deplete any of ribosomal RNA, mitochondrial RNA, globin transcripts, or others. Notably, the heteroduplexes may form at positions along the RNA molecule that do not form any regular, repeating, or uniform pattern or spacing.

BRIEF DESCRIPTION OF THE DRAWINGS

FIG. 1 diagrams a method of probe design according to certain embodiments.
FIG. 3 shows a distribution of inter-probe gap sizes.
FIG. 7 describes an example of a method of probe design.

DETAILED DESCRIPTION

Figure 2:
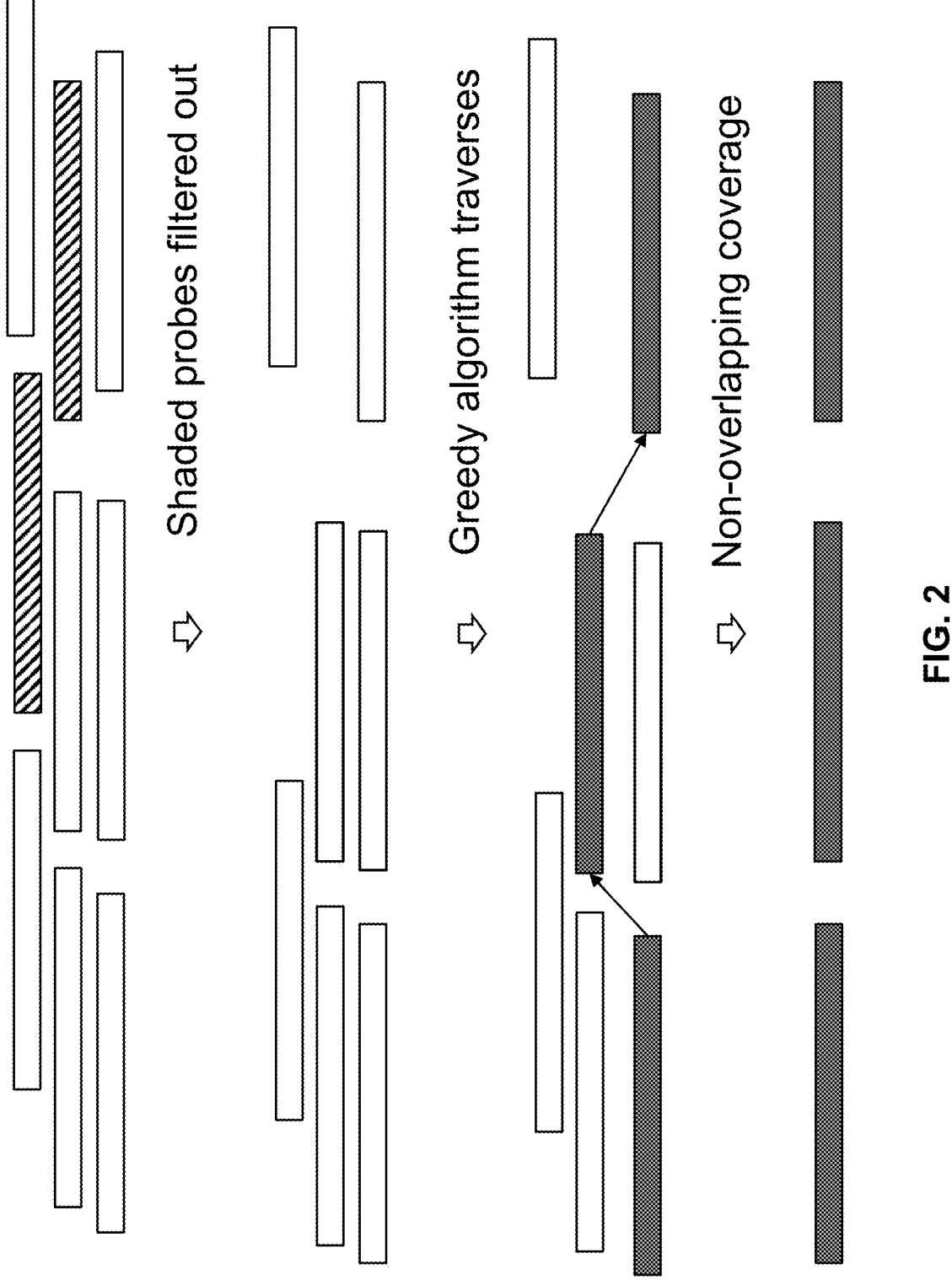
FIG. 2 shows steps of a method of probe selection.

The disclosure relates to methods for designing and using RNA depletion probes as well as probe sets designed according to such methods. Methods and materials of the disclosure are useful to remove species of RNA molecules from a sample. Methods of the invention have particular applications in transcriptomics and certain RNA-based workflows intended to identify or quantify certain populations of RNA molecules. For example, it is often the case that there is a need to isolate specific RNA molecules, e.g. mRNA, in a sample. Depletion probes of the invention are useful to deplete, for example, ribosomal catalytic RNA (that do not themselves code for proteins) that might interfere with detection of the target mRNA in the sample. As an example, one approach to isolating and evaluating mRNA is to use poly-A-specific priming with oligo-dT as one approach to avoiding rRNA molecules. However, the rRNA is still present and interfering and there are a variety of workflows that benefit from using target capture other than poly-T primer hybridization to mRNA poly-A tails. Moreover, partially-degraded samples, such as formalin-fixed paraffin embedded (FFPE) samples frequently have separation of the 3'poly-A tail from the 5' end of the transcript, which makes information from the 5' ends inaccessible with techniques relying on poly-A enrichment. In addition, certain RNA species, such as long non-coding RNA (lncRNA) do not contain poly-A tails. In such examples, the in ability to deplete non-target RNA makes detection of target more difficult.

Methods and compositions of the invention provide tools for depleting any RNA species out of a sample. RNA depletion according to embodiments of the invention operates by the use of "depletion probes" or DNA oligos designed to hybridize to the RNA molecules to be depleted. The DNA oligos anneal to the RNA to form heteroduplexes. RNase H recognizes DNA-RNA heteroduplexes and cleaves the RNA in a heteroduplex. RNA depletion using RNase H is appealing because it does not require that the RNA to be preserved contains poly-A tails and is indifferent to the presence of poly-A tails on the RNA molecule targeted for depletion. Thus, even arbitrary mRNA transcript, such as a globin may be depleted by RNase H depletion. In addition, methods of the invention permit lncRNA and mRNA enrichment even in highly-degraded samples.

According to the invention, RNase H depletion utilizes depletion probes, short DNA oligos that hybridize to the RNA to be depleted, forming heteroduplexes. Some conventional approaches use a set of depletion probes that tile along an RNA molecule. The use of tiled probes is appealing due to the possibility that the entire target molecule is covered. Other approaches have been suggested that allow certain spacing between probes, such as leaving an inter-probe gap of some specific number of bases between each adjacent pair of probe targets. Moreover, some depletion probe sets may include probes that are described as overlapping one another, apparently offering super-coverage (e.g., coverage>1). In such description, "overlap" is a recognized term but the word choice is misleading to the extent it describes two probes hybridizing to a single target molecule with one of them leaving an un-bound single-stranded end where the other probe is fully bound. In actual use it is just as possible that each of the so-called overlapping probes will find independent copies the same type of target RNA molecule and each fully bind to one molecule. Here, the word overlap (and as used herein) simply acknowledges that the DNA oligos are designed against complementary regions where, for two oligos, it is their cognate targets that overlap.

Regardless of the probe tiling strategy, whether abutting, uniformly spaced, or overlapping, existing probe designs reveal a design paradigm in which one decides which coverage pattern appears best suited and applies that coverage pattern to cover the molecule to be depleted. The coverage pattern may mandate that the probe targets overlap, abut, or have regular spacing. Once the pattern is selected, it is applied to the molecule to design the probes, which are synthesized and used for RNA depletion.

The invention recognizes that conventional probe coverage strategies create laboratory reagents that impose limitations on their use in analytical assays. For example, due to the variety in GC content, or due to RNA secondary structure, existing depletion probe sets can be used only under very limited conditions. Also, optimizing the reaction temperature for a majority of the probes means that the reaction is performed at a temperature too high or too low for some of the probes. Conventional probe coverage strategy is not well suited to potential regions of sequence similarity between the RNA to be depleted and the RNA of interest.

The invention addresses such limitations. The invention provides methods of probe design that rely first on biophysical properties of the molecules being deleted and those being preserved. Methods of the invention use sequence data for RNA molecules and also use reference RNA data, and apply modeling to predict probes that hybridize to target RNA without marking for destruction the mRNA to be preserved.

Probes are designed on the basis of biophysical properties. Methods and compositions of the invention use sequence information, GC richness, reference sequences, and modeled/predicted biochemistry behaviors to generate and select probe sets that perform well, with uniform, consistent hybridization throughout the probe set and also without off-target hybridization. A significant insight of the invention is that probe design does not require a spatial pattern that is projected indiscriminately onto the length of an RNA molecule. Instead, desired properties, such as a range of melting temperatures, are established and then sets of probes are designed having those desired properties. For example, a meta-set comprising all possible probes with the desired properties may be generated algorithmically, e.g., from sequence data, and then that meta-set may be reduced based on mapping, filtering, and/or scoring to select a smaller but useful set of probes. The selected set of useful probes is synthesized as DNA oligos and used to deplete the selected RNA from a sample, thus enriching for the RNA of-interest. Significantly, a reference data set of sequences of the non-target RNA may be used in, e.g., a filtering or scoring step, to remove probes from the meta set that would deplete possibly scarce mRNAs of interest from the sample.

In initial steps of generating all or a substantial number of possible probes, some embodiments start by establishing a nearly uniform Tm (or Tm range) between any probe and its target, and also aim to minimize the Tm between each probe and any potential off-targets.

A number of approaches may be used to arrive at the file set. The selected probes preferably bind across the target RNA. Algorithms may be used to seek a probe set that binds across all regions of the target (e.g., 45S, mitochondrial rRNA, or globin transcripts). Certain embodiments use graph-based algorithms that seek to minimize (with no specific constraints) the spacing between probes, and the potential Tm with off-targets (e.g., possibly estimated by percent homology with the strongest non-target BLAST hit). Other target spanning algorithms may be used to arrive at a set of probes. A probe set may be supplemented in part one or more additional rounds of similar design, and/or by hand based on empirical data. For example, some probes may be "boosted" in concentration to improve performance, e.g., based on results in initial test assays.

Using such methodologies, the invention provides methods of making depletion probes, sets of the depletion probes, and methods of using the depletion probes RNaseH-based depletion of rRNA and other high expression RNAs from, for example, RNA-Seq libraries. Any suitable analytical package or algorithm may be used in probe design. Preferred embodiments generate the candidate probes in a manner that is informed by sequence information of the target as well as a set of reference RNA sequence information for the sample or organism (as an interesting aside, it does not matter if the algorithm uses a reference RNA sequence data set that also includes the target). The disclosure provides probe design methods, and probe sets that are designed by methods that are systematic and rational and that allow rapid design iteration to optimize performance of the probes set.

At least three fundamental approaches to designing probes are contemplated. A first approach makes use of Bloom filters for identification of unique k-mers (Bloom filtered). A second approach generates a set of probes with balanced melting temperature (Tm) that is filtered by a basic local alignment search tool (e.g., BLAST or related algorithms) to avoid creating probes that deplete non-target RNAs (BLAST-filtered). A third approach generates a set of probes with balanced melting temperature (Tm) then uses BLAST to score probes then selects a probe set that traverses the target RNA while minimizing score (BLAST-scored).

In these approaches, potential probes may be screened for uniqueness against RefSeq human RNA (manually masked for targeted sequences). In certain exemplary embodiments, RNA28SNx and RNA18SNx were used as development models. Probes against other RNAs, such as 5S and mitochondrial rRNA probes, may be designed similarly. After the initial set of probes are generated, a final candidate set that covers the target may be selected, e.g., using bioinformatics programming techniques known to the skilled artisan. Preferred embodiments employ the BLAST-scored methodologies.

FIG. 1 diagrams a BLAST-scored method 101 of probe design according to certain embodiments. The method begins by selecting a target and obtaining sequence data. This can be performed by accessing a publicly available database of genetic information such as GenBank or Ensemble. For example, the method 101 may be used to deplete the Homo sapiens 18S ribosomal N3 RNA from a biological sample. A computer system of the invention may be used to retrieve NCBI reference sequence NR_146152.1. A software package such as BioPerl or BioRuby may be used to import sequence data, such as the RNA18SN3 FASTA file for 18S ribosomal RNA N2 stored at GenBank under NCBI reference sequence NR_146152.1. This file may be brought into the system and set as the target. The system may be operated to bring in multiple targets (e.g., essentially simultaneously, e.g., in one "run"). Preferred embodiments set at least two or three RNA molecules each as a target, such as the longest ribosomal RNAs plus a globin transcript.

Having set the target, the method 101 involves setting boundaries for melting temperature. This may be done by setting a target temperature and then allowing a range, such as 50 degrees plus or minus 3. The system then examines the target file to generate all possible strings that, if synthesized as DNA oligos, would have a Tm within bounds. In one straightforward embodiment, a software package on the computer system begins at the 5' end of the target file and reads each possible k-mer, calculating tm for each. Any suitable calculation may be performed. In some embodiments, the system uses [4(G+C)+2(A+T)]. To illustrate with a trivial example, NR_146152.1 begins with a T. So the first possible k-mer is a 1-mer consisting of T. The calculation returns 2, which is out of bounds (not within 3 degrees of 50), so the system does not write the k-mer to a file. The system then reads the 5' 2-mer (which is TA), and so on. Every string that yields a T m within bounds is written to a file, and then the system moves to position 2 in the target file.

For this stage it may be preferred to have established a minimum (and/or maximum) length. The system iterates over the target file and writes all possible k-mers with Tm in bounds to a target file, e.g., all in-bounds probes may be written to a FASTA file.

The method may proceed to BLAST each probe against reference RNA sequence data. In one straightforward example, BLAST scores are used to simply omit probes that match non-target RNA above some threshold. In certain embodiments, the BLAST result is used to score the probes (e.g., [0.1]), where the score will be used as a cost in a cost function. The computer system performing the operation may preferably use blastn-short.

The BLAST score may be used to filter probes out or to assign a score to probes that is used by an algorithm that selects a set of probes to cover the target RNA.

The algorithmic task for the computer system is to cover the target RNA (for convenience, from 5' end to 3' end), a task that can be presented to the computer as traversing a graph where the probes are nodes and any inter-probe gaps are edges (or, trivially, vice-versa). The system attempts to traverse the graph, using any score as a cost function for using that probe. This may be performed using a version of the Dijsktra algorithm in which edge weights become the "distance" between two nodes+the "cost" for visiting the target node. In some embodiments, an edge weight includes a gap opening value and a separate gap extension value. In some other embodiments the cost of visiting a node may be the based its similarity to potential non-target RNAs.

FIG. 2 diagrams steps of a method of probe selection. In the top panel, all probes have been generated, e.g., a GenBank file is read for all strings of certain length calculated to have a Tm within bounds, which strings are written to a FASTA file. In the diagram, each rectangle is a candidate probe, a sequence from the GenBank file. The hatch-marked blocks are the probes that will be eliminated by BLAST comparison to reference RNA sequence data. The reference matching probes are eliminated from consideration (directly removed in BLAST filter, effectively avoided in BLAST score), and an algorithm seeks to construct a directed graph through the probes. Any suitable algorithm may be used. Certain embodiments use a graph traversal algorithm that essentially looks for a directed acyclic graph with an optimized cost, where nodes and edges are assigned some cost. In the BLAST scoring embodiments, reference-matched probes (hatch-marked in FIG. 2) end up having a relatively high cost. Because edges may have costs proportional to length, the algorithm may seek to minimize gaps (as drawn, the rectangle "probes" are nodes and the arrows are edges). The nodes along the found path are the probe set that is selected. In this algorithm, the selected probe set offers non-overlapping coverage of the target RNA molecule.

Graph algorithms are known in the art and conducive to sequence analysis due to a natural fit between the linear nature of genetic information carried in nucleic acid sequences and the linear nature of a path through a directed graph. Graph platforms (such as Neo4J) are appealing here because they cross over a software/hardware barrier. Software packages can read from, write to, and query (e.g., traverse) data stored as graphs, but the graph storage makes non-standard use of computer hardware. For example, some graph platforms use index-free adjacency in which a graph query reads nodes, but the nodes contain references to the physical locations in the physical memory at which adjacent nodes are written so that traversal moves to the referenced location in hardware. This is in comparison to relational databases that use lookup index tables written in familiar software to document relationships, with index-free adjacency using spatial addresses on hardware in such a way as to be much faster than index tables. Because algorithms of the disclosure are conducive to implementation in graph platforms, methods of the disclosure potentially run very fast and can scale up to query any arbitrary sized reference target and BLAST the FASTA probes against any arbitrary sized reference set without any difficulty.

In exemplary embodiments, a cost function to traverse the graph was set to k*score^r (k, r parameters can be specified from the command line but default to k=256, r=2). Effectively, k is equal to the distance penalty that would be paid by leaving a gap of sqrt(k) bases when score=1 (worst possible scenario). In the cost function, r defines the rate at which the score penalty decreases, such that larger values of r mean that small differences/small amounts of mismatch are treated more liberally. The graph traversal minimizes the costs function and the visited nodes become the probe set. The probes associated with a graph traversal with an optimal score (not necessarily absolute minimum) are used.

FIG. 3 shows a distribution of inter-probe gap sizes for different values of k in the cost function. Increasing values of k appear to decrease overall BLAST scores of probes, with a potential tradeoff in overall coverage. Probe sets may be reviewed manually. For example, a biologist may select k=1000 because any matches to off-target RNA get very expensive scores, so the resulting probe set will not deplete rare mRNAs, even though it may leave a 28 base gap (final number of the k=1000 line in the figure) of ribosomal RNA un-depleted after RNase H digestion.

Thus the software package initially parses the target sequence to generate a set of probes (candidate sequences complementary to the RNA molecule within predicting melting temperature boundaries), BLASTs the probes to assign a cost function to each of the candidate sequences based at least in part on a match score to the reference off-target RNAs, and find a cost-minimizing directed graph through the probes (candidate sequences) to thereby select a set of probes that map to positions along the RNA molecule. As discussed, the set is selected by an algorithm that minimizes cumulative cost function, inter-position gaps, and overlap. The described algorithm does not literally minimize overlap, but simply avoids it. Other algorithms are within the scope of the disclosure. In fact, overlap does not necessarily need to be avoided as it is not to be assumed that so-called overlap probes actually compete for binding to the same one copy of a molecule. Using the method 101, the probes are selected by a computer system to provide DNA oligos that each uniquely anneal to the RNA molecule, preferably with minimal or no overlap, and with minimal or no annealing to off-target RNA.

A second method of probe design, BLAST-filter, is also within the scope of the invention. In BLAST filter embodiments, a computer system may be used to first generate all probes within a given Tm window using, e.g., an input target RNA sequence file and a Perl script. In any embodiments, the probe length may be set to have a default, e.g., 21, but that can also be varied, e.g., a different value can be used, the value could be switched on-the-fly, or a range of values may be set. Similarly, temperature parameters may be varied. E.g., some embodiments use a script that permits a 3.0 degree variance around an initial value (i.e. if the min and max length don't permit generating a probe with the Tm initial value, then script will generate the next closest candidate that is within 3.0 degrees—this can be adjusted or eliminated). To generate all probes, they are designed by finding the first probe of desired Tm starting from every base from the 5'. An additional strategy useful in any embodiments to ensure nothing is lost at the 3' end, has the script also produce probes from the 3' end 250 bases in. In various preferred embodiments, the script uniquifies the initially generated probe set.

In this BLAST-filter embodiment, the system will BLAST probes with blastn-short against RefSeq—target sequences. Filter out probes with a percent identity above a given threshold. Results show that this strategy gives results with some similarity to the Bloom filter methodologies. These BLAST-filtering methodologies may be used to generate probes with the strictest possible identity criteria.

Any suitable approach may be used to generate a probe set. An insight of the invention is that information about biochemical properties of target and off-target RNA is used first, to generate a probe set that will actually perform the intended task of depleting target RNA and leaving off-target RNA. Having generated probes according to biophysical properties, then the practitioner may apply other criteria (e.g., a cost function to the Dijsktra algorithm that minimizes gaps) that promote results similar to the chief purpose of prior art probe design strategies (no gaps). Any suitable approach that uses biophysical properties may be used, such as the Bloom-filter, BLAST-filter, or BLAST-score methods presented here. Methods of the invention provide probe sets that tend to have certain characteristic features.

Certain features of probe sets designed according to methods of the invention are characteristic and worthy of note. For example, probe spacing is highly variable and appears random (sequence of gaps below). Some probes abut one or more other probes (i.e. 5' end touches 3' end of another probe and/or 3' end touches 5' end of another probe). Some probes overlap another probe (note comments elsewhere about overlap). Many gaps exceed 30 nucleotides (max=111, see FIG. 4). Probes have variable length (min=18, max=44, see FIG. 5). The Tm of the probes are largely uniform, mostly falling into two discrete groups (in general we found that probes targeting GC-rich segments needed to have a higher Tm than those targeting more balanced segments). Coverage of all targets is not end-to-end. In fact coverage of the 45S rRNA is missing 5 nucleotides at the 5' end and 47 nucleotides at the 3' end. Probes are not present in the mix at equimolar concentrations—some are boosted up to 10× to improve performance (based on empirical data).

Some of those features are contrary to accepted wisdom about depletion probes. For example, in prior art probe designs, gaps of 30 and even 111 bases are rare and thought to be something to be avoided. Additionally, un-ordered mixtures of gaps, abutments, and overlaps were treated as something to avoid. Significantly, uniformity of length is sacrificed and probes of the invention have variable length and substantially uniform melting temperature. Because probes of the disclosure are designed first from biophysical properties, they outperform prior art probes (e.g., substantially uniform Tm ensures consistent digestion by RNase H because intended heteroduplexes will all be stable under similar conditions whereas in prior-art strict tiling strategies, the probes and targets in AT-rich regions may melt apart). A consequence of the design paradigm is that probe spacing is highly variable and appears random.

Strategies of the disclosure have distinct advantages. For example, there is a reduced need to denature targets and/or probes—allowing a reduction in workflow. The invention eliminates need to add enzyme while reaction mix is being heated—likely due to more efficient denaturation of off-target probe binding. Together, those reductions cut workflow time down by half compared to competitors, with no apparent loss in data quality.

Figure 4:
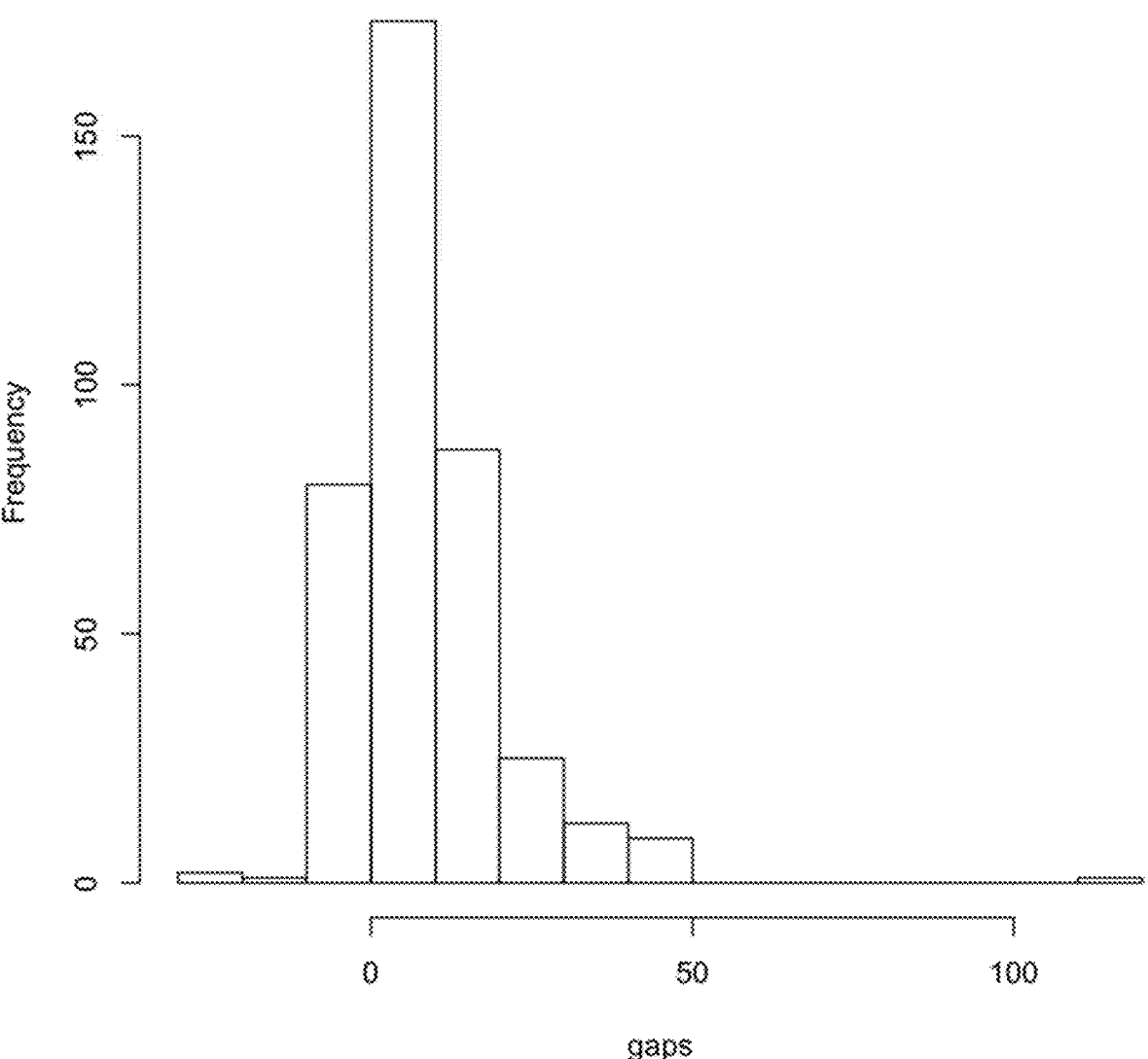
FIG. 4 is a histogram of gap sizes.

FIG. 4 is a histogram of gap sizes on that were determined for one specific RNA. As discussed, probe spacing is highly variable and appears random. A set of probes was designed against the specific RNA. The following is the sequence of inter-probe gap sizes where the probes form heteroduplexes with the specific RNA (negative values indicate an overlap): 7, 10, 10, 10, 1, 9, 29, 18, 14, 15, 3, 21, 0, 0, 0, 7, 12, 17, 2, 1, 2, 3, 2, 33, 6, 18, 16, 34, 6, 9, 11, 2, 19, 3, 20, 11, 1, 6, 18, 12, 10, 13, 11, 13, 17, 6, 6, 8, 16, 14, 19, 10, 0, 11, 8, 2, 14, 5, 7, 8, 3, 9, 11, 21, 0, 3, 17, 12, 7, 13, 14, 15, 18, 1, 1, 0, 2, 3, 11, 4, 13, 18, 19, 6, 5, 5, 14, 1, 0, 0, 18, 19, 13, 15, 6, 12, 3, 111, 1, 1, 46, 21, 12, 12, 8, 11, 12, 9, 0, 1, 7, 3, 2, 0, 14, 9, 0, 7, 7, 20, 0, 7, 1, 3, 1, 1, 0, 0, 1, 0, 10, 3, 3, 26, 4, 11, 9, 10, 1, 2, 1, 5, 0, 0, 5, 19, 7, 17, 10, 5, 6, 0, 3, 8, 5, 0, 6, 6, 6, 7, 13, 5, 29, 0, 21, 29, 3, 7, 5, 12, 7, 8, 12, 0, 9, 4, 7, 9, 5, 34, 3, 13, 10, 9, 9, 4, 22, 36, 15, 26, 29, 8, 14, 17, 4, 44, 12, 11, 47, 9, 10, 9, 28, 25, 15, 0, 19, 22, 15, 37, 14, 12, 33, 5, 29, 39, 45, 7, 41, 25, 13, 32, 33, 10, 16, 39, 0, 0, 3, 18, 24, 7, 20, 7, 4, 3, 0, 0, 0, 0, 0, 0, 0, 0, 0, 0, 0, 0, 0, 0, 0, 25, 0, 0, 0, 0, 0, 0, 0, −28, 19, 10, 0, 0, 0, 16, 0, 4, 14, 10, 10, 22, −9, 0, 18, 4, 0, 0, 3, 8, 2, 4, 14, 8, 2, 2, 6, 3, 5, 8, 8, 25, 25, 14, 4, 5, −8, 2, 13, 12, 16, 2, 2, 5, 9, 6, 2, 9, 6, 10, 11, 3, 8, 4, 4, 4, 5, 3 3, 0, 0, 0, 3, 0, 10, 0, 4, 0, 0, 0, 0, 5, 10, 0, 0, 0, 0, 9, 6, 13, 0, 1, −9, 8, 12, 13, 26, 11, 9, 45, −16, −5, −25, 4, 0, 18, 11, 0, 34, 14, 1, 0, 0, 0, 0, 1, 4, 8, 1, 0, 3, 5, 22, 14, 37, 11, 16, 9, 7, 0, 45, 10, 6, 16, 45, 22, 0, 28. There is no evident uniformity or pattern. The probe set was not designed to form a pattern along the molecule.

Similarly to the gap sizes, probe length is variable.

Figure 5:
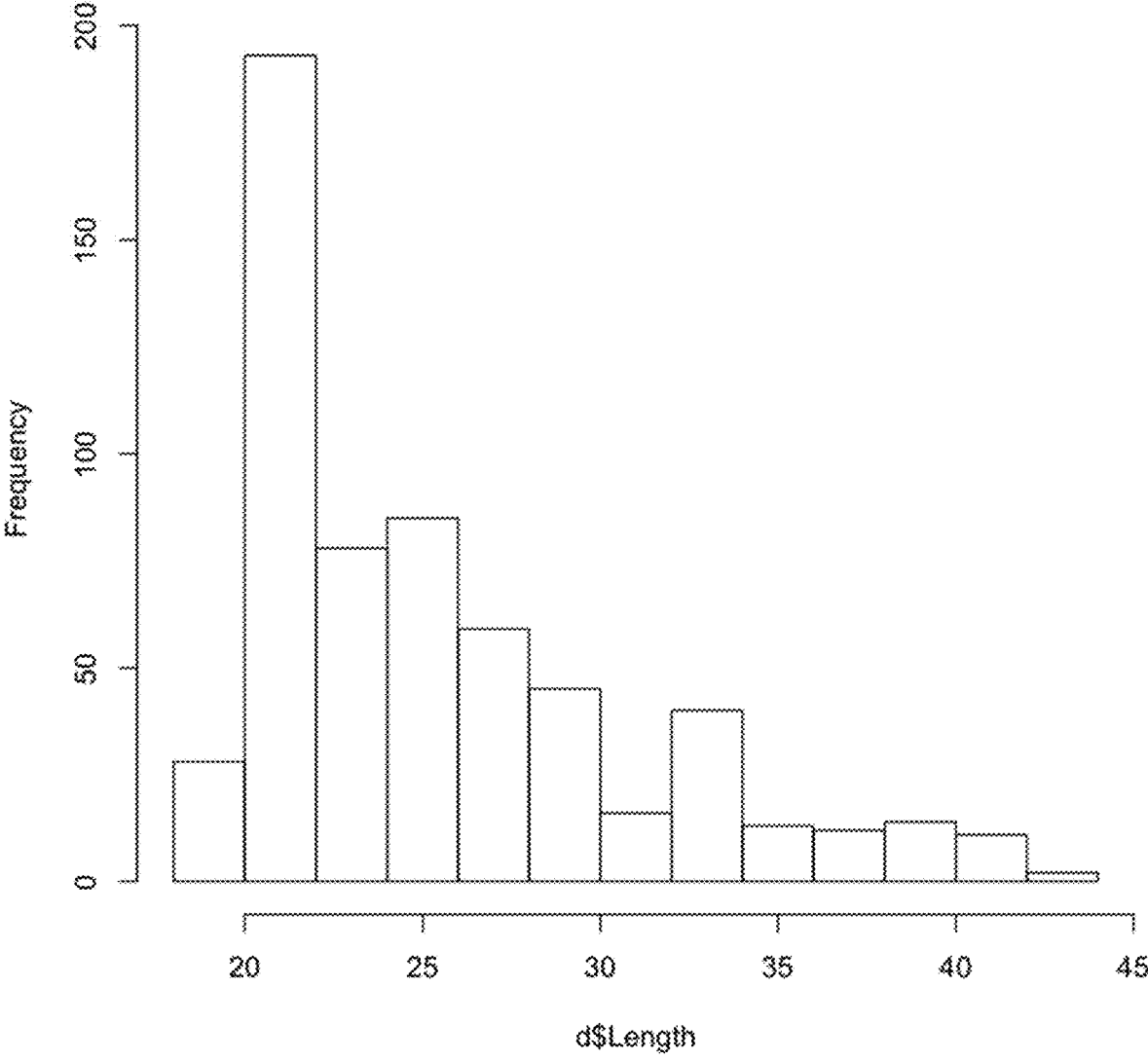
FIG. 5 is a histogram of probe lengths.

FIG. 5 gives a histogram of probe lengths for the set designed against the specific RNA (where d$Length is probe length). The histogram of gaps and the histogram of probe lengths reveal important properties of probe sets of the invention. The gaps are not uniform. In fact, the distribution of gaps is not regular or standard.

Note from the histogram that there is at least one gap above 100. The mode is likely zero. Also, there are negative values. Similarly, the probe lengths include at least one at 44 and an apparent mode just above 20. The histograms exhibit such patterns because the probes were not designed to a gap or length specification. In fact, biophysical properties may inform not just sequence selection but also probe length. For example, high GC oligos may be allowed to be made at the higher end within the Tm boundaries, but also may be made shorter than low GC oligos. Algorithmically, the system may seek to minimize spacing between adjacent heteroduplexes, yet nevertheless give such a histogram (with a >100 value).

Using probes of the disclosure, one may perform RNA depletion by hybridizing a plurality of DNA oligos to a target RNA molecule(s) in a sample to form heteroduplexes, wherein the DNA oligos have sequences selected to (i) give the heteroduplexes melting temperatures within a predetermined range, and (ii) minimize matches to reference off-target RNAs; and digesting RNA in the heteroduplexes. These steps may be performed within a single-cell RNA-Seq (scRNA-Seq) workflow. E.g., the method may include isolating single cells into a fluid partition, releasing nucleic acid from the cell within the partition (e.g., by chemical or thermal cell lysis), and depleting the target RNA molecule (s). The fluid partition may be a droplet, e.g., in an emulsion or microfluidic device, or a well, e.g., in a plate such as a multiwell plate or picotiter plate. The method may include introducing reaction reagents (e.g., any of lysis reagents, depletion probes of the invention, RNase H, capture oligos, primers, template-switching oligos, tagmentation reagents, reverse transcriptase, dNTPs, etc.) at droplet formation, by pipetting into wells, or by droplet merger. Any of the primers or oligos may include barcodes, sequencing adaptors, universal priming sites, etc. For example, in some embodiments, every RNA transcript is captured by an oligo that includes a unique or nearly-unique sequence to function as a unique molecular identifier and every cDNA is given a partition- or cell-barcode.

Using depletion probes of the invention, heteroduplexes are formed and may exhibit a non-uniform distribution along the RNA molecule. The RNase H digests the target RNA. Preferably the DNA oligos (i.e., the depletion probes) have been tested and shown not to hybridize stably to protein coding transcripts in a standardized human reference RNA extract. After digestion, superabundant RNAs such as ribosomal or globin are substantially removed. Remaining transcripts are copied into cDNA (optionally barcoded by molecule and/or cell). Downstream method steps may further copy or amplify the cDNA molecules. For example, the cDNA molecules may be amplified to create a sequencing library, e.g., with sequencing adaptors such as Illumina Y-adaptors at ends of the library members.

Methods described herein are useful to provide a set of RNA depletion probes that includes a plurality of DNA oligos able to hybridize to a target RNA molecule to form heteroduplexes. The DNA oligos have sequences selected to (i) give the heteroduplexes melting temperatures within a predetermined range, and (ii) minimize matches to off-target RNA. Preferably the heteroduplexes will form with a non-uniform distribution along the RNA molecule, e.g., spacing between the heteroduplexes may be highly variable and/or mathematically random. The probes may be designed algorithmically, even automatically, by a computer system operable for generating a set of candidate sequences complementary to the RNA molecule with predicting melting temperatures within the predetermined range; assigning a cost function to each of the candidate sequences based at least in part on a match score to the reference off-target RNAs; and selecting a set of the candidate sequences that map to positions along the RNA molecule, wherein the set is selected by an algorithm that minimizes: cumulative cost function, inter-position gaps, and overlap. The computer system may output the selected set as any suitable file such a FASTA file, a file formatted for input into an oligonucleotide synthesis instrument, or in a format accepted by a commercial oligonucleotide vendor such as Integrated DNA Technologies (IDT). Even in some embodiments, the computer system may include an application programming interface that selects the probe set and transmits a well-formed IDT order over internet protocols. The probe set, once synthesized, may be provided in packaging for use in a laboratory or for shipping or sale. For example, the probe set may be lyophilized in a tube or in solution in a tube, where a tube can be any suitable tube such as a 1.5 mL microcentrifuge tube such as those sold under the trademark EPPENDORF. The probe set may then be used in methods of performing RNA depletion as described above.

As described above, the probe set may be selected by methodologies that use Bloom filters, BLAST filters, or BLAST scoring. Preferred BLAST scoring embodiments are detailed above. A Bloom filter embodiment is described in the examples. Besides the Bloom filter, BLAST filter or BLAST score methodologies, or any other suitable methodology may be used to provide depletion probes. The invention provides sets of RNA depletion probes, short DNA oligos that hybridize along the length of a target RNA and mediate digestion of the target RNA by RNase H to remove super-abundant RNA molecules from a sample. Depletion probes according to the invention are designed foremost based on biochemistry and the biophysical properties of the probes so that all of the depletion probes of a set exhibit substantially uniform, consistent behavior in binding to a target RNA in a sample. Probes are principally designed to specific performance targets and biophysical properties, yielding probe sets with irregular, even essentially random, spacing along a target RNA molecule.

EXAMPLES

Example 1. Bloom Filters

Figure 6:
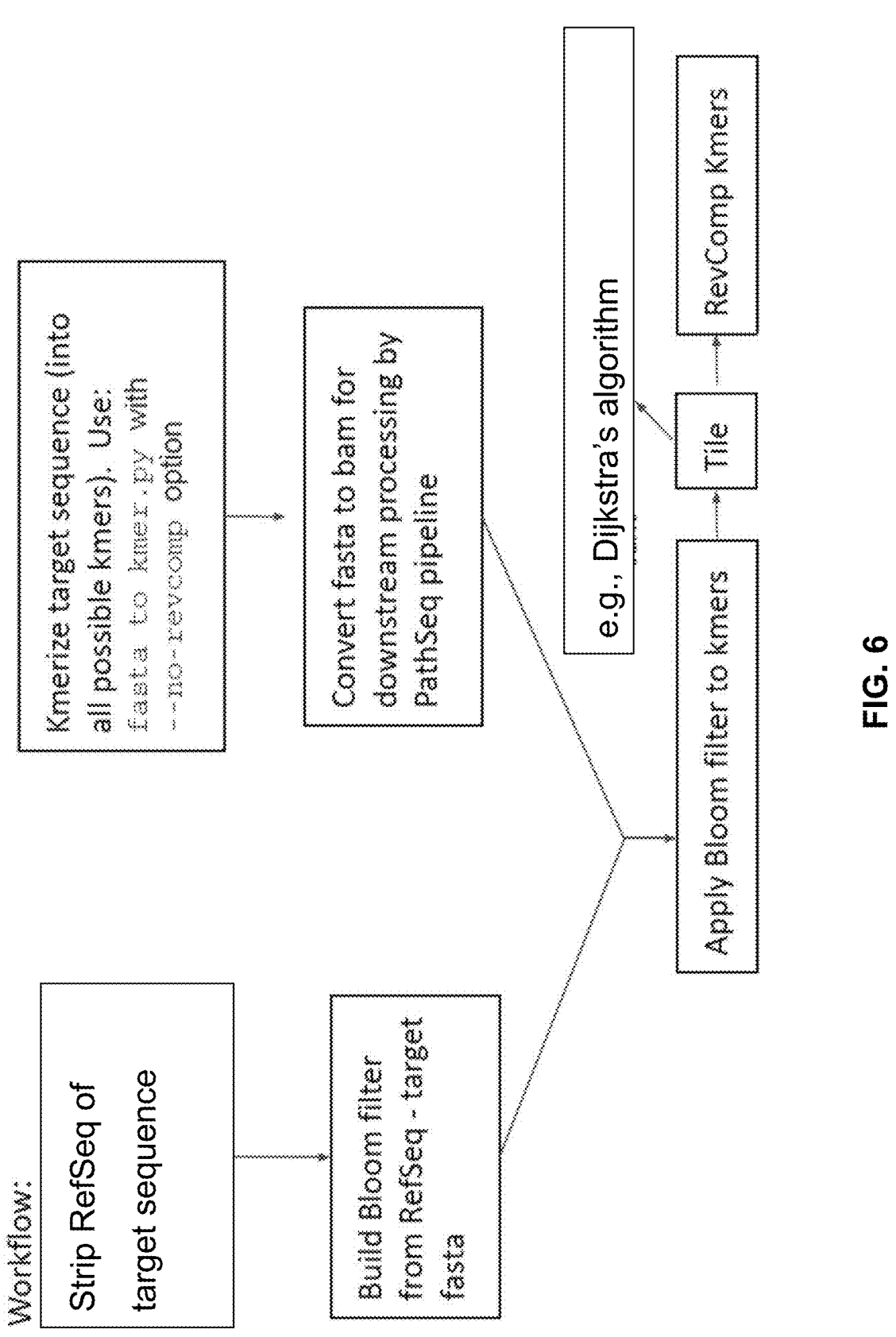
FIG. 6 diagram a Bloom filter design methodology.

FIG. 6 diagram a workflow for a Bloom filter design methodology. The workflow begins with setting a target RNA and having a RefSeq data set. For example, a package such a BioPerl may be used to open a handle to the most current version of RefSeq as it was described in Pruitt, 2007, NCBI reference sequences (RefSeq): a curated non-redundant sequence database of genomes, transcripts and proteins, Nucleic Acids Res 35(Database):D61-5, incorporated by reference. The target RNA is stripped out of (or masked off in) the RefSeq.

Additionally, the target is kmerized, or parsed into kmers such as all possible kmers. For the skilled artisan it is trivial to write a script such a Perl script that writes all possible kmers to a FASTA file. Depending on platform, it may be preferable to convert the FASTA file to a binary alignment map (BAM) for downstream processing, e.g., by the PathSeq pipeline.

Using a Bloom filter, search kmers from RefSeq in target. This may be performed using the PathSeq GATK pipeline to build a Bloom Filter package that identifies kmers present in a target sequence, that are not present elsewhere in RefSeq.

A Bloom filter is a space-efficient probabilistic data structure useful to test whether an element is a member of a set. False positive matches are possible, but false negatives are not. An empty Bloom filter is a bit array of m bits, all set to 0. There must also be k different hash functions defined, each of which maps or hashes some set element to one of the m array positions, generating a uniform random distribution. Typically, k is a small constant which depends on the desired false error rate $\varepsilon$, while m is proportional to k and the number of elements to be added. To add an element, feed it to each of the k hash functions to get k array positions. Set the bits at all these positions to 1. To query for an element (test whether it is in the set), feed it to each of the k hash functions to get k array positions. If any of the bits at these positions is 0, the element is definitely not in the set; if it were, then all the bits would have been set to 1 when it was inserted. If all are 1, then either the element is in the set, or the bits have by chance been set to 1 during the insertion of other elements, resulting in a false positive. In a simple Bloom filter, there is no way to distinguish between the two cases, but more advanced techniques can address this problem. See Najam, 2019, Pattern matching for DNA sequencing data using multiple Bloom filters, Biomed Res Int 14:7074387, incorporated by reference.

The Bloom filter is applied to the kmers. For example, the Bloom filter may be used to simply exclude kmers that are found in RefSeq. Alternatively, the Bloom filter may be used to find kmers in RefSeq and to assign scores to those (e.g., some constant times % match or some other such arbitrary score).

With the set of kmers in a file or data structure, the system tiles a set of the kmers across the target RNA. This may be performed as a graph traversal, which is well suited to performance by computers even for large (including very, very large) data quantities due to the unique way graph platforms such as Neo4J access hardware, e.g., with index-free adjacency. The system tiles the RNA sequence. Tiling an (RNA) sequence can be stated as the problem of traversing a directed graph where edges have cost. In some embodiments, initially the cost of an edge is the distance (in bases) between the end of probe and the beginning of the next. The lowest cost path from the beginning of the RNA to the end can be most efficiently (and optimally) calculated using Dijkstra's algorithm (see e.g., Rodriguez-Puente, 2013, Algorithm for shortest path search in geographic information systems by using reduced graphs, Springerplus 2:291, incorporated by reference). Dijkstra runs in $O[|V|+|E|*log(|V|)]$. Using the simple heuristic of only considering probes that live within a fixed distance of each other (as opposed to all to all), $|V|\in O$ ($|V|$)—so the runtime complexity is $O[|E|*log(|E|)]$.

Dijkstra's algorithm was implemented in a general fashion that allows it to operate on any graph object, for which the nodes can hold any data type. It is noted that in the first implementation of the tiling algorithm, the graph was constructed such that the distance from probe x to probe y is start(y)-stop(x). This works, but Dijkstra is a greedy algorithm, and may leave gaps at the end of the tiling path (i.e. when there are multiple optimal solutions, it will pick one where the costs are incurred late in the optimization, and it generally accumulates these in longer stretches). This is fixed relatively easily by setting the distance between nodes to be: $[start(y)-stop(x)]^2$, so that the cost grows faster when a single gap is extended relative to opening a number of short gaps. Additionally or alternatively it may be suitable to assign a gap extension penalty distinct from a gap formation penalty.

It is noted that the graph algorithm may read from initial probe candidates that cover every base in target (e.g., RNA18SN3) yet leave long stretches uncovered. For RNA18SN3, all filtered 21-mer covers all but 4 bases, yet two Dijkstra tilings leave 223 and 222 bases uncovered, respectively. Because the probes are non-overlapping and there is only one probe starting at each position, filtering out the probes makes it highly unlikely that a contiguous coverage path can be found. Interestingly this need not be a restriction on applicability and the resulting probe set may be used for RNA depletion. It is noted that with the existing algorithm, when using an unfiltered sets of probes (i.e. when every possible probe is fed into the tiler) the return is an optimal path with just a small coverage gap at the end (if the length of the tiled sequence is not a multiple of the length of the probes, which are all fixed in this case). Inputs that contain a proper tiling return the same input. Manual curation of results may be helpful but manual curation of results appears to confirm that suitable results are obtained.

Example 2. Design Workflow

FIG. 7 describes an example of a method of Human/Mouse/Rat (H/M/R) probe design. The method includes: algorithmic design of depletion probes to human transcript target; removing probes with high homology to undesired human transcript targets; algorithmic design of depletion probes to mouse/rat transcript targets; removing probes with high homology to undesired mouse/rat transcript targets; cross checking human probes to mouse/rat transcriptome and vice versa; and remove probes with high homology to undesired transcript targets in H/M/R. After such design methodology, the final probe set may be synthesize and used to deplete unwanted RNA from a sample or packaged for storage, shipping, distribution, or later use. For example, the probes may be placed in a tube or vial, in an aqueous solution or lyophilized for later reconstitution. Such vial or tube may optionally include other reagents such as RNase H.

Example 3. Results

Figure 8:
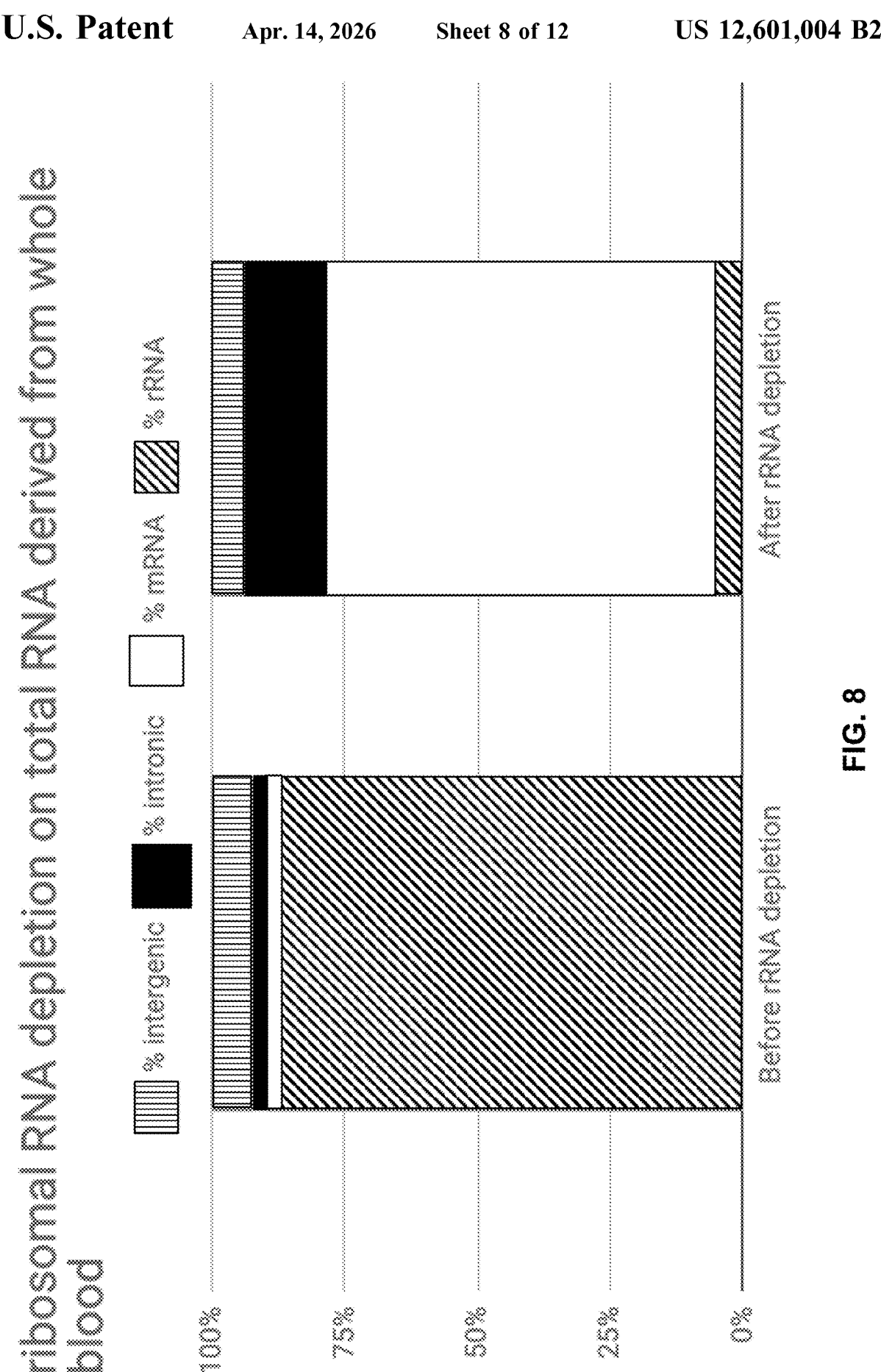
FIG. 8 shows ribosomal RNA depletion from whole blood.

FIG. 8 shows ribosomal RNA depletion on total RNA derived from whole blood. The left bar, "before RNA depletion", shows that the sample was >80% ribosomal RNA. After rRNA depletion, as shown by the bar on the right, the sample was <5% rRNA and approximately 75% mRNA. Thus these results show that probe sets and methods of the disclosure are effective for removing ribosomal RNA from samples.

Figure 9:
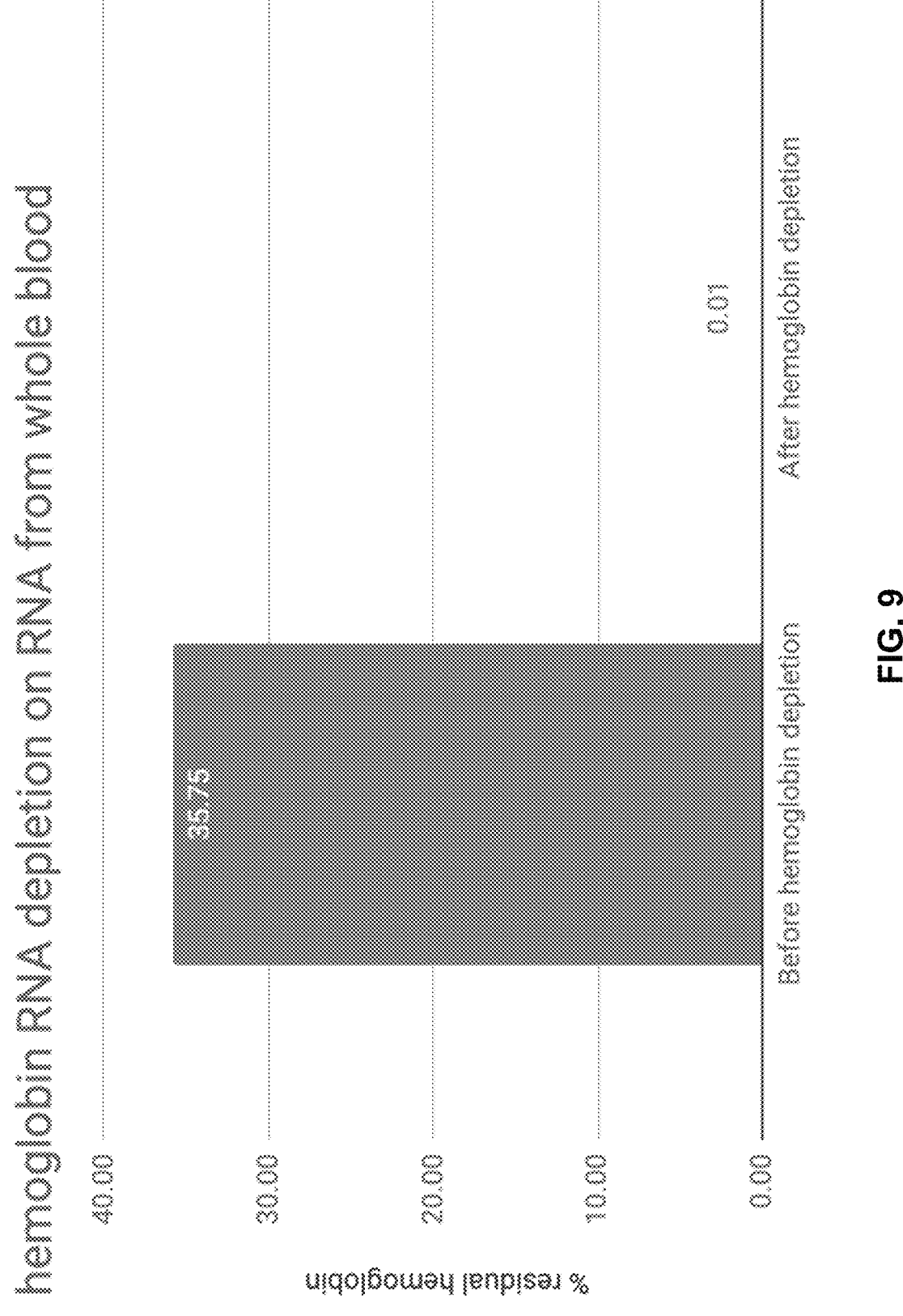
FIG. 9 shows the result of hemoglobin RNA depletion from whole blood.

FIG. 9 shows the result of hemoglobin RNA depletion from whole blood using a probe set and methods of the disclosure. Before hemoglobin depletion, as shown by the bar on the left, the sample included about 35.75% residual hemoglobin RNA. After depletion, the sample included about 0.01% residual hemoglobin RNA. Thus these results show that probe sets and methods of the disclosure are effective for removing hemoglobin RNA from samples.

Figure 10:
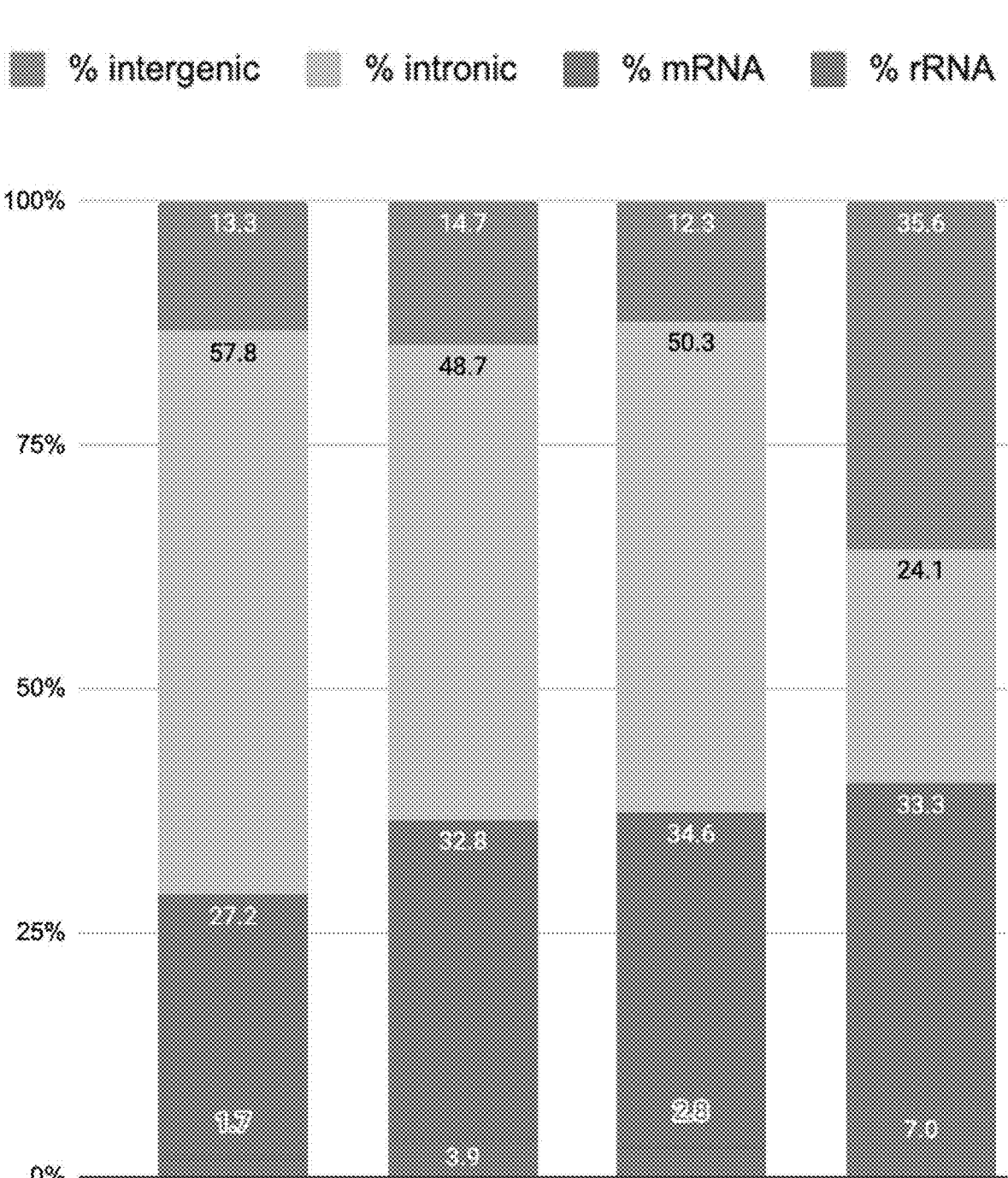
FIG. 10 shows rRNA depletion from formalin-fixed, paraffin embedded (FFPE) tissue with 10 ng RNA.

FIG. 10 shows that methods and probe sets of the invention are useful for robust ribosomal RNA depletion from total RNA samples derived from formalin-fixed, paraffin embedded (FFPE) tissue with 10 ng RNA.

Figure 11:
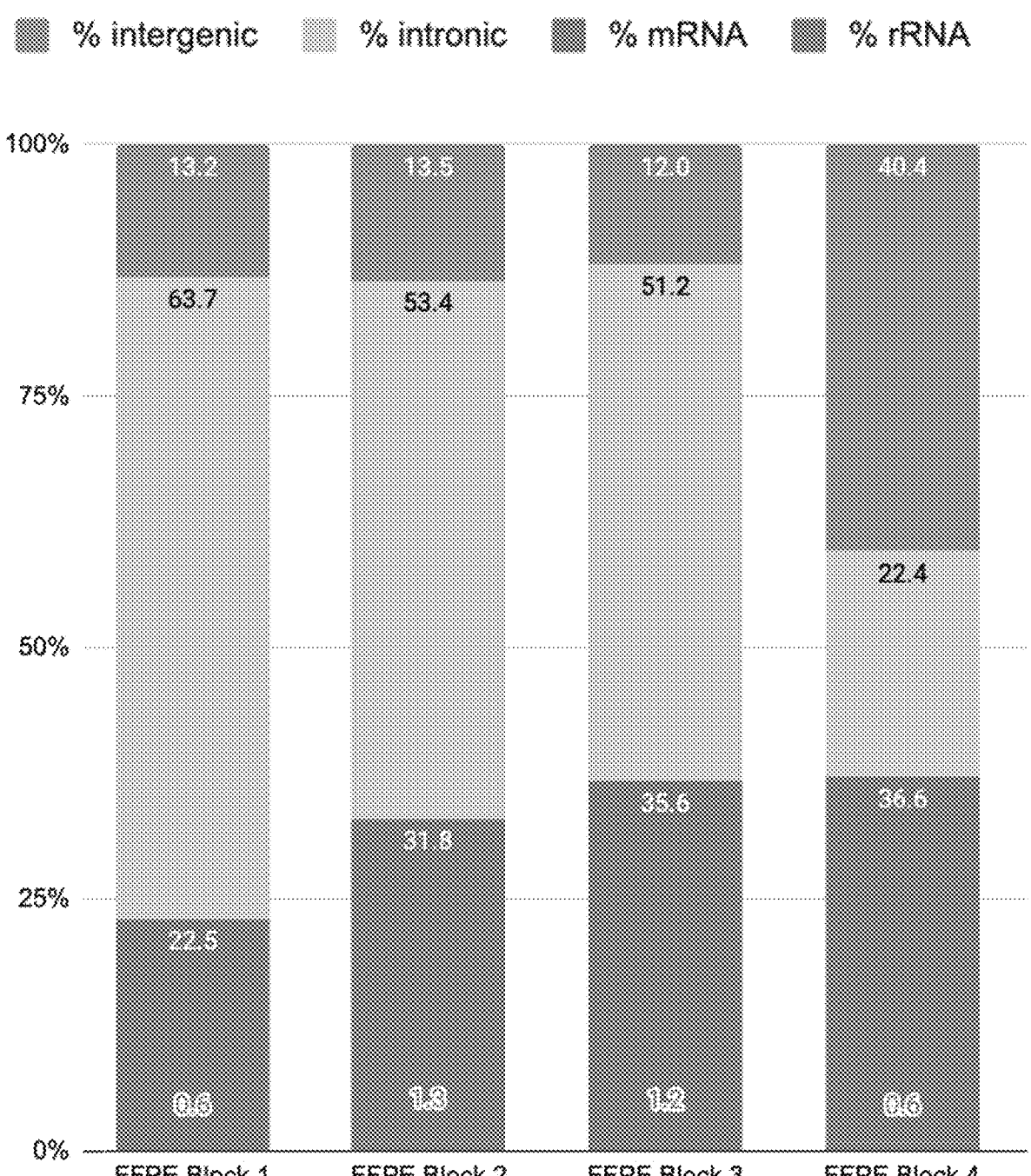
FIG. 11 shows rRNA depletion from FFPE tissue with 400 ng RNA.

FIG. 11 shows results from FFPE with 400 ng RNA.

For 4 blocks each, with 10 ng and 400 ng total RNA per block being obtained, in all cases, % ribosomal RNA after depletion was lower than or equal to about 7% and, in most cases, was significantly lower than 5%. Thus these results show that probe sets and methods of the disclosure are effective for removing RNA from FFPE samples.

Figure 12:
FIG. 12 shows rRNA depletion from universal mouse and rat references.

FIG. 12 gives quantitative results of ribosomal depletion from total RNA derived from universal mouse and rat references. Using methods and probe sets of the invention, the mouse sample was depleted, from about 85% ribosomal RNA down to about less than %% ribosomal RNA. The rate sample had about 80% ribosomal RNA original and methods and probe sets of the invention depleted the rat sample down to less than about 5% ribosomal RNA. Thus these results show that probe sets and methods of the disclosure are effective for removing RNA from rat or mouse samples.

What is claimed is:

1. A method of depleting a target RNA transcript in a sample, the method comprising contacting the sample with:
   a nuclease that recognizes DNA/RNA heteroduplexes and cleaves the RNA; and
   a plurality of DNA oligos that are each complementary to the target RNA transcript and have minimal to no annealing to off-target transcripts, wherein:
   the sequences of the DNA oligos of the plurality of DNA oligos are selected by:
      (i) generating a set of candidate sequences complementary to the target RNA transcript, wherein the candidate sequences have a predicted melting temperature within a 3.0 degree variance around an initial value;
      (ii) removing from the set of candidate sequences, candidate sequences that do not have minimal to no annealing to off-target transcripts; and
      (iii) selecting from the set of candidate sequences, sequences of the plurality of DNA oligos using a cost function to minimize gaps between adjacent DNA/RNA heteroduplexes formed by the target RNA transcript and the plurality of DNA oligos,
      wherein the DNA oligos of the plurality of DNA oligos are present in the sample at non-equimolar concentrations;
      wherein the plurality of DNA oligos form DNA/RNA heteroduplexes with the target RNA transcript in the sample and gaps between the DNA/RNA heteroduplexes are 0-111 nucleotides.

2. The method of claim 1, wherein the nuclease that recognizes DNA/RNA heteroduplexes and cleaves the RNA is an RNase H.

3. The method of claim 1, comprising combining the sample, the nuclease that recognizes DNA/RNA heteroduplexes and cleaves the RNA, and the plurality of DNA oligos before a hybridization incubation step or a digestion incubation step.

4. The method of claim 1, wherein the target RNA transcript comprises a ribosomal RNA, a globin transcript or mitochondrial RNA.

5. The method of claim 1, wherein the plurality of oligos form DNA/RNA heteroduplexes with the target RNA transcript and the mode of the distribution of nucleotide distances between the DNA/RNA heteroduplexes on the target RNA transcript is zero.

6. The method of claim 1, wherein each oligo of the plurality of DNA oligos is at least 18 bases in length.

7. The method of claim 1, wherein each oligo of the plurality of DNA oligos is 18-44 bases in length.

8. The method of claim 1, wherein each oligo of the plurality of oligos anneals to the target RNA transcript.

9. The method of claim 1, further comprising selecting sequences of the oligos, wherein the selecting comprises:
   generating a set of candidate sequences complementary to the target RNA transcript, wherein the candidate sequences have a predicted melting temperature within 3° C. of each other;
   assigning a cost function to each of the candidate sequences based at least in part on a match score to reference off-target RNAs; and
   selecting, from the candidate sequences, sequences of the oligos of the plurality of DNA oligos that minimize the cost function, inter-position gaps, and overlap.

10. The method of claim 1 comprising depleting an additional target RNA transcript in the sample, the method further comprising contacting the sample with an additional plurality of DNA oligos that are each complementary to and specific to the additional target RNA transcript, wherein:
   (i) each oligo of the plurality of DNA oligos and each oligo of the additional plurality of DNA oligos has a melting temperature within 3° C. of each other; and
   (ii) the additional plurality of oligos comprises oligos that are complementary to different regions of the additional target RNA transcript, wherein distribution of nucleotide distances between the different regions is non-uniform.

11. The method of claim 3, wherein the target RNA transcript and the additional target RNA transcript are selected from a ribosomal RNA, a globin transcript, and/or a mitochondrial RNA.

12. The method of claim 3, wherein each oligo of the plurality of DNA oligos is 18-44 bases in length.

* * * * *